United States Patent [19]

Helmut et al.

[11] Patent Number: 4,482,719
[45] Date of Patent: Nov. 13, 1984

[54] PROCESS FOR OBTAINING 3-CYANOPYRIDINE

[75] Inventors: Beschke Helmut, Hanau; Dahm Ludwig, Alzenau; Friedrich Heinz, Hanau, all of Fed. Rep. of Germany

[73] Assignee: Degussa Aktiengesellschaft, Frankfurt, Fed. Rep. of Germany

[21] Appl. No.: 391,434

[22] Filed: Jun. 23, 1982

[30] Foreign Application Priority Data

Jul. 22, 1981 [DE] Fed. Rep. of Germany ....... 3128956

[51] Int. Cl.$^3$ .......................................... C07D 213/57
[52] U.S. Cl. .................................................... 546/286
[58] Field of Search ........................................ 546/286

[56] References Cited

FOREIGN PATENT DOCUMENTS 862011 1/1953 Fed. Rep. of Germany ...... 546/286

Primary Examiner—Alan L. Rotman
Attorney, Agent, or Firm—Cushman, Darby & Cushman

[57] ABSTRACT

The gaseous mixture resulting from the catalytic reaction of 3-methylpyridine with ammonia and oxygen is treated with water to recover 3-cyanopyridine. The treatment takes place in two steps. In the first step there is used a temperature of about 30° to 60° C. and in the second step at a temperature about 10° to 30° C. lower than in the first step.

20 Claims, 1 Drawing Figure

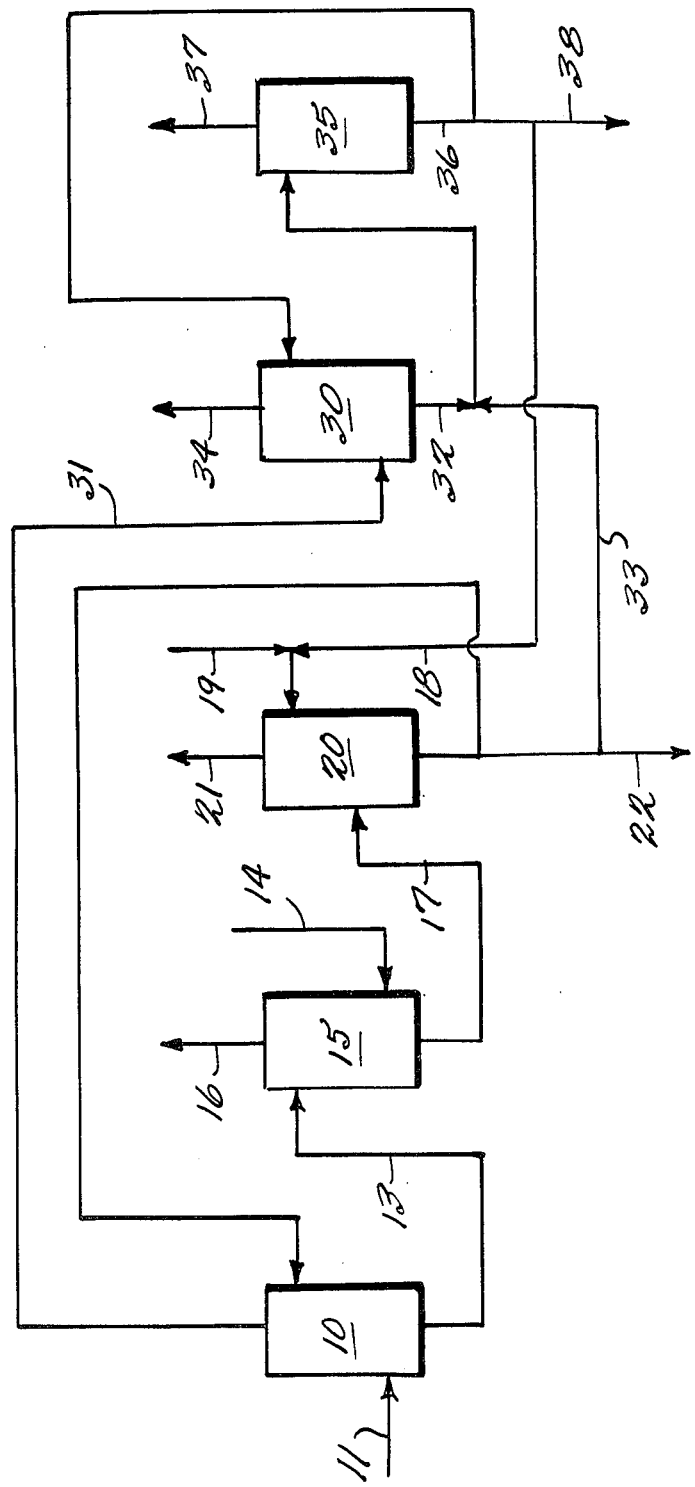

PROCESS FOR OBTAINING 3-CYANOPYRIDINE

BACKGROUND OF THE INVENTION

The invention is directed to a process for the recovery of 3-cyanopyridine from the gaseous mixture resulting from the catalytic reaction of 3-methylpyridine with ammonia and oxygen.

There are known numerous processes for the production of 3-cyanopyridine by the catalytic reaction of 3-methylpyridine with ammonia and oxygen in the gas phase. These processes differ essentially in the catalysts used. For example, there can be employed as catalysts tin vanadate in admixture with phosphorus pentoxide on aluminum oxide, silica gel or their mixture (Japan published application No. 42-6066) or molybdenum oxide in admixture with oxides of vanadium, chromium, manganese or cobalt on aluminum oxide, magnesium oxide, silica or titanium dioxide (Japan published application No. 45-13572) or pure vanadium pentoxide of specific surface area and particle size (German OS No. 2435344). Especially suited are catalysts which are produced by pretreating by heating to temperatures of 600° to 1100° C. in the presence of oxygen mixtures which contain at least one of the elements titanium, iron, copper, cobalt, manganese and nickel and in a given case, a carrier (German Pat. No. 2039497 and related Lüssling U.S. Pat. No. 3,927,007). The entire disclosure of the Lussling U.S. patent is hereby incorporated by reference and relied upon.

The gaseous mixtures formed in the catalytic reaction generally contain, independent of which catalyst is used, 3-cyanopyridine, ammonia, in a given case, unreacted 3-methylpyridine and byproducts such as water, carbon dioxide, nicotinamide, and hydrogen cyanide. The working up is essentially directed to obtaining the 3-cyanopyridine as well as the recovery of excess ammonia and the unreacted 3-methylpyridine. In order that the ammonia can be returned to the cycle and used again, it is necessary to separate it from carbon dioxide and the remaining byproducts.

In a known process for the production of 3-cyanopyridine by catalytic rreaction of 3-methylpyridine the reaction mixture is cooled with dry ice, the part condensed thereby is washed with a solvent such as benzene, and the 3-cyanopyridine and the 3-methylpyridine present, in a given case, recovered from this solution by distillation (U.S. Pat. No. 2,861,999). In another process the reaction mixture is washed with water, the aqueous solution extracted with ether, and the 3-cyanopyridine recovered by distillation off of the ether (Great Britain Pat. No. 777,746. In regard to the recovery of the excess ammonia, it occurs in both cases as an aqueous solution, nothing is said. The recovery is expensive and might not be without considerable loss.

In further process the reaction mixture is washed with methanol at low temperature and in this manner the 3-cyanopyridine, in a given case the 3-methylpyridine present, and some ammonia separated (German OS No. 2,435,344). In this process the main portion of the ammonia remains in the residual gas. However, it is disadvantageous that this also contains byproducts, such as especially carbon dioxide, which are enriched and disturb the reaction if the residual gas is repeatedly recirculated.

SUMMARY OF THE INVENTION

There has now been found a process for recovering 3-cyanopyridine from the gaseous mixture resulting from the catalytic reaction of 3-methylpyridine with ammonia and oxygen by the treatment with water characterized by first treating the gaseous mixture at temperatures of 30° to 60° C. and then at temperatures which are about 10° to 30° C. lower than the first temperature. In this way there is not only recovered pure 3-cyanopyridine but also the ammonia and the 3-methylpyridine present in a given case separated off and recovered in such manner that these materials can be recirculated directly and without loss.

According to the process of the invention the 3-cyanopyridine can be recovered from all gaseous mixtures which are obtained in the customary catalytic reactions of 3-methylpyridine with ammonia and oxygen in the gas phase, especially from the gaseous mixtures which are formed in the reaction using the catalysts of German OS No. 2039497 (and related Lüssling U.S. Pat. No. 3,927,007) and German OS No. 3107755 (and related Beschke U.S. application Ser. No. 351,402, filed Feb. 23, 1982, Degussa Docket 1076, entitled "Catalysts for the Production of 3-Cyanopyridine").

Disclosure of the Beschke Application Ser. No. 351,402:

BACKGROUND OF THE INVENTION

The invention is directed to a process for the production of 3-cyanopyridine by catalytic reaction of 3-methylpyridine with ammonia and oxygen at elevated temperature. It is particualrly directed to catalysts for this purpose made of compounds of the elements antimony, vanadium, and oxygen and at least one of the elements iron, copper, titanium, cobalt, manganese, and nickel, as well as the process for producing the catalyst.

There are known several processes for the production of 3-cyanopyridine from 3-methylpyridine through its reaction with ammonia and oxygen at elevated temperature in the gas phase. They differ through the reaction conditions and especially through the catalysts. Among the processes and catalysts only those are suitable for use on an industrial scale which show good selectivity and simultaneously result in high space-time-yield.

It is known to use as catalysts for the reaction of alkylpyridines to cyanopyridines tin phosphate with addition of compounds of the elements molybdenum, bismuth, vanadium, iron or cobalt (German AS No. 1770841) This process in the case of the reaction of 3-methylpyridine to 3-cyanopyridine only results in moderate yields, moreover, at slight selectivity.

Besides it is known to employ as catalysts tin vanadate in admixture with diphosphorus pentoxide or aluminum oxide, silica gel or their mixture (Japan published No. 42-6066) or molybdenum oxide in admixture with oxides of vanadium, chromium, manganese, or cobalt on aluminum oxide, magnesium oxide, silicon oxide, or titanium oxide (Japan published No. 45-13572) or pure divanadium pentoxide of specific surface area and particle size (German OS No. 2435344). These processes, it is true result in relatively favorable yields at good selectivity but they require reaction gases which are greatly diluted with air. Therefore, there are obtained only small space-time-yields.

Furthermore, it is known to use catalysts which are produced from mixtures which contain antimony and vanadium in the atomic ratio of from 1.1:1 to 50:1 and at least one of the elements iron, copper, titanium, cobalt, manganese, and nickel and in a given case a carrier material and are prepared by heating to a temperature of 600° to 1100° C. in the presence of oxygen (German Pat. No. 2039497 and related Lussling U.S. Pat. No. 3,923,819, the entire disclosure of which is hereby incorporated by reference and relied upon). It is true that in this manner high space-time-yields are produced, however, the selectivity of the catalyst is unsatisfactory.

SUMMARY OF THE INVENTION

There have now been found catalysts for the reaction of 3-methylpyridine with ammonia and oxygen to form 3-cyanopyridine consisting of compounds of the elements antimony, vanadium, and oxygen and at least one of the elements iron, copper, titanium, cobalt, manganese, and nickel whereby the atomic ratio of antimony to vanadium is greater than 1, which are characterized by containing in addition to these compounds a lattice layer silicate and highly dispersed silica and have a BET surface area of 5 to 50 m$^2$/g, a macropore volume of 0.1 to 0.8 cm$^3$/g and an average pore radium of 1 to $8 \times 10^{-7}$ cm. These catalysts show an excellent selectivity and give good yields and good space-time-yields. They are outstandingly suited for use on an industrial scale. Especially advantageous are catalysts which contain antimony, vanadium, and titanium.

For the production of the catalyst of the invention there are used antimony and vanadium as well as the elements iron, copper, titanium, cobalt, manganese, and nickel suitably as compounds with oxygen, in the elemental form or as compounds which can be converted into compounds with oxygen, such as ammonium salts of oxygen acid or nitrates.

The proportions are so chosen that in the catalysts the atomic portion of antimony is greater than that of vanadium. The atomic ratio of antimony to vanadium is suitably between 1.1 to 1 and 50 to 1, preferably between 1.1 to 1 and 25 to 1. As atomic ratio of antimony to iron, cobalt, copper, manganese, and nickel, individually or collectively, there is used 2 to 1 up to 20 to 1, preferably 3 to 1 up to 10 to 1. However, the atomic portion of iron, cobalt, copper, manganese, and nickel individually or collectively, should not exceed the portion of vanadium. As atomic ratio of antimony to titanium there are suited 1 to 3 to 8 to 1, preferably 1 to 2 up to 4 to 1.

There is added to the so composed catalyst materials of the invention a mixture of a lattice layer silicate and highly dispersed silica so that in the catalysts their portion is about 10 to 60 weight percent, preferably 20 to 40 weight percent. The ratio of lattice layer silicate to highly dispersed silica in parts by weight is about 20 to 1 to 0.25 to 1, preferably 10 to 1 to 1 to 1.

Lattice layer silicates occurring in nature for use in the invention generally require a pretreatment. The silicate is finely powdered and, suitably under continuous movement, for example, in a rotary tubular furnace or fluidized bed furnace, heated to a temperature between 900° and 1200° C. The heating time depends on the type of lattice layer silicate, the temperature and the type of furnace. In most cases the material is held at a temperature within the range mentioned for at least one hour but not over 10 hours. Preferably there is used as the lattice layer silicate montmorillonite and for this the treatment time is from 4 to 6 hours at 975° to 1050° C.

The highly dispersed silica can be obtained in any desired manner, for example, by pyrolysis of silicon compounds, e.g. silicon tetrachloride, or trichlorosilane or by precipitation from solution of silicon compounds, e.g. sodium silicate. Suitably it has a BET surface area of about 50 to 500 m$^2$/g, preferably from 100 to 300 m$^2$/g.

For the production of the catalysts of the invention the starting materials are intensively mixed in the finest possible distributed form. It has proven advantageously hereby to add water and in a given case to introduce one or more of the substances as a solution or suspension in water. There are added to the mixtures molding aids as well as pore formers in the most finely divided form possible and if necessary additional liquids, also in a given case carrier materials.

As molding aids and pore formers there are used the materials customarily employed for this purpose, as molding aid for example, graphite, stearic acid, or polyethylene powder. As pore former for example, urea, ammonium carbonate, or carbohydrates such as saccharides, e.g. sugar, starch, or cellulose. The molding aid suitably is present in an amount of 1 to 15 weight percent, preferably 2 to 10 weight percent of the catalyst mixture and the pore former is suitably present in an amount of 0.1 to 50 weight percent, preferably 0.5 to 40 weight percent.

Besides water there are chiefly used water miscible organic solvents, especially polyhydric alcohols such as glycol or glycerine or also mixtures of these liquids. The content of liquid of the catalyst mixture is suitably about 10 to 35 weight percent, preferably 15 to 30 weight percent.

The preferred methods of operation for the preparation of the catalyst mixtures are either first to insert antimony or antimony trioxide into nitric acid and to treat at the boiling temperature and then to add divanadium pentoxide or ammonium vanadata and the other elements, these being added as the nitrate or the titanium as titanium dioxide, as well as the lattice layer silicate and the highly dispersed silica and to again treat the entire mixture at the boiling temperature or to add these materials simultaneously to nitric acid and to treat at the boiling temperature finally, in a given case after neutralization of the acid, to bring the mixtures to dryness and to heat to a temperature about 280° to 300° C. The molding aid and the pore former are added to the thus treated mixtures and, if necessary, after grinding the mixture to particles below 0.5 mm, the liquid added.

The catalyst mixtures are then pressed to briquettes whose size is suitably between about 1 and 8 mm. For this purpose there are used customary devices, for example, tabletting machines or extruders. Especially suited are granulate forming machines, especially cog wheel granulate forming machines.

The briquettes are treated in the presence of oxygen at a temperature between about 350° and 900° C., preferably between 500° and 800° C.

The finished catalysts generally have a BET surface area of about 5 to 50 m$^2$/g, a macropore volume of about 0.1 to 0.8 cm$^3$/g, and an average pore radius of about 1 to $8 \times 10^{-7}$ cm. Its bulk density is about 0.9 to 1.4 kg/l. According to their shape and size they are used in fixed bed or in fluid bed reactors.

The reaction of the 3-methylpyridine with ammonia and oxygen to form 3-cyanopyridine takes place in customary manner in the gas phase. There is suitable a wide range of reaction conditions. The reaction is chiefly carried out without the use of pressure or under slight excess pressure up to about 3 bar at a temperature between about 320° and 460° C., preferably at a temperature between 340° and 440° C. It is advantageous besides to mix steam into the gases. The ratio of 3-methylpyridine to ammonia, oxygen, or air and in a given case steam can be chosen within wide limits. Generally it is suitable to use per mole of 3-methylpyridine, about 2 to 10 moles, preferably 3 to 8 moles of ammonia, about 20 to 40 moles, preferably 25 to 35 moles of air and about 2 to 10 moles, preferably 3 to 8 moles of steam. Per liter of bulk volume of catalyst per hour there is suitably fed into the reactor about 1 to 2 moles of 3-methylpyridine.

In the examples all parts and percent are by weight unless otherwise indicated.

The compositions can comprise, consist essentially of the stated materials and the process can comprise, consist essentially of, or consist of the recited steps with such materials.

DETAILED DESCRIPTION

Example 1

23.3 kg of antimony trioxide, 4.7 kg of ammonium metavanadate, 12.8 kg of titanium dioxide, 11.7 kg of montmorillonite, and 5.8 kg of highly dispersed silica having a surface area of 200 m$^2$/g were suspended in 140 liters of water. Then there were added 16.4 liters of 54% nitric acid. The mixture was slowly heated to the boiling temperature, treated with 7 liters of water and held for 2 hours at the boiling temperature, then adjusted to a pH of 4.6 with ammonia, cooled, dried on a roller drier, heated in a tubular rotary drier to 300° C. and ground in a spike mill to a particle size below 0.5 mm. 4500 grams of the thus prepared catalyst mixture was intensively mixed with 225 grams of graphite and 1700 grams of a 20% aqueous urea solution and then shaped to extruded briquettes having a diameter of 3 mm. The briquettes were heated in the air stream and held hereby for 15 hours at 120° C., for 2 hours at 550° C., 1 hour at 650° C., and 3 hours at 770° C. The bulk density of the catalyst was 1.05 kg/l, the BET surface area 18 m$^2$/g, the macropore volume 0.28 cm$^3$/g and the average pore radius 2.7×10$^{-7}$ cm.

1050 grams of the catalyst were filled into a reaction tube having a clear width of 20 mm and a length of 3000 mm. In homogeneous flow there were fed into the tube hourly 1.34 moles of 3-methylpyridine* 6 moles of ammonia, 30 moles of air and 6 moles of steam. The gas mixture was supplied preheated to the reaction tube. The tube was heated by a salt melt which was held at 350° C. Upon leaving the reaction tube the gases were washed with water. In the course of 8 hours on the average 94% of the 3-methylpyridine employed reacted. The yield of 3-cyanopyridine on the average, based on the 3-methylpyridine employed was 89 mole % and the space-time-yield 124 g/1×h.

* with a gas mixture which contained per mole of 3-methylpyridine

Example 2

The same catalyst and procedure were used as in Example 1 but the salt melt was held at 360° C. In the course of 8 hours, there was an average reaction of 96% mole % and the space-time-yield 129 g/1×h.

Example 3

The same catalyst and procedure were used as in Example 1 but the salt bath temperature was held at 365° C. and there were fed in hourly 1.47 moles of 3-methylpyridine with the gas mixture. In the course of 8 hours the average reaction was 94%, the yield of 3-cyanopyridine 90 mole % and the space-time-yield 137 g/1×h.

Example 4

The same catalyst and procedure were used in Example 1 but the salt melt was held at 365° C. and a gas mixture fed in which only contained 4 moles of ammonia per mole of 3-methylpyridine. In the course of 8 hours the average reaction was 93%, the yield of 3-cyanopyridine 80 mole % and the space-time-yield 124 g/1×h. Referring again to the present invention which as stated can be employed in recovering 3-cyanopyridine from all gaseous mixture obtained in the customary catalytic reactions of 3-methylpyridine including those with the catalysts of Beschke U.S. Application Ser. No. 351,402 to carry out the process of the invention the warm gaseous mixture suitably directly after leaving the reactor in the presence of water in a first step is brought to a temperature of about 30° to 60° C., preferably to a temperature of about 35° to 55° C., and in a second step to a temperature of about 10° to 30° C., preferably to around 15° to 25° C. lower than the first temperature. Hereby the pressure can be selected substantially at random, but it is recommended to operate at normal pressure or only moderately lowered or elevated pressures. Such pressures occur in a given case by the gases being sucked through the plant or forced through by pressure.

Preferably the gaseous mixture in the first step as well as in the second step is brought to the temperatures mentioned by washing it with aqueous wash liquids. However, if the gaseous mixture leaving the reactor contains water vapor (steam) in amounts which are sufficient for the formation of an aqueous solution in which the 3-cyanopyridine, the 3-methylpyridine present in a given case, as well as the carbon dioxide and other byproducts can be taken up, it is only needed to cool the gaseous mixture in the first step.

Although pure water is usable as wash liquid in the first step, generally it is suitable to employ water which contains ammonia. In what amounts and with what content of ammonia the wash liquid is used depends, in a given case, on the composition of the gaseous mixture to be treated, chiefly on its content of water, ammonia and carbon dioxide. In most cases, especially in a continuous method of operation, in which the wash liquid is recirculated, it is suitable to use as wash liquid water which is substantially or completely saturated with ammonia at the temperature in question. It is advantageous to so regulate the washing liquid that per mole of carbon dioxide in the gases to be treated there is present at least about 3 moles, preferably at least about 5 moles of ammonia and per mole of ammonia about 0.1 to 0.5 liter of water. In the second step as wash liquid there is employed as washing liquid water which is free of ammonia or at all events, has a small content of ammonia. The wash liquid suitably is so regulated that per mole of ammonia in the gaseous mixture to be treated in the second step there is present at least about 0.2 liter of water.

The aqueous solution obtained in the first step contains the 3-cyanopyridine, the unreacted 3-methylpyridine present in a given case, ammonia, the carbon dioxide, namely this as ammonium bicarbonate, as well as the remaining byproducts, insofar as they are soluble in the medium. The aqueous solution obtained in the second step contains ammonia.

For the recovery of the 3-cyanopyridine and in a given case, the 3-methylpyridine from the aqueous solution obtained in the first step, this is extracted with an organic solvent. As solvents there can be used for example, aliphatic chlorinated hydrocarbons, e.g. methylene chloride, chloroform, carbon tetrachloride, 1,2-dichloroethane, or 1,1-dichloroethane or aromatic hydrocarbons, e.g. benzene, toluene, or xylene, or in a given case, chlorinated aromatic hydrocarbons, e.g. chlorobenzene or dichlorobenzene.* The extract is fractionally distilled. The solvent recovered hereby can be employed for further extractions.

*Benzene is preferred.

The aqueous solution remaining after the extraction besides ammonia contains ammonium bicarbonate. The carbon dioxide is desorbed from this solution by treating the solution, suitably under addition of water, under pressures of about 5 to 12 bar, preferably 6 to 10 bar, at temperatures of about 120° to 170° C., preferably of 130° to 160° C. The carbon dioxide escapes with portions of water. It is generally advantageous to drive off carbon dioxide and water to such an extent or to supply water to such an extent that there results a residual solution which contains about 2 to 10 moles, preferably 3 to 8 moles, of ammonia per liter of water and at most about 0.4 mole, preferably at most 0.3 mole, of carbon dioxide per mole of ammonia. This type of residual solution is generally suited directly for employment as wash liquid in the first step.

The aqueous solution obtained in the second step for the recovery of ammonia is desorbed at temperatures of about 80° to 140° C., preferably of 90° to 130° C., and pressures of about 1.5 to 3.0 bar, preferably of 1.8 to 2.7 bar. Generally the ammonia resulting hereby can be led back directly and used for new reactions and the water freed from ammonia can be employed as wash liquid in the second step.

BRIEF DESCRIPTION OF THE DRAWING

A preferred form of the invention which is especially suited for a continuous operation is shown in schematic form in the single FIGURE of the drawing.

DETAILED DESCRIPTION

The gases leaving the reactor through line 11 were led in the first step into a gas washer 10 for the washing. The gas washer is operated at 30° to 60° C. The residual solution from desorption unit 20 as wash liquid goes through line 12 to this washer 10. The aqueous solution flowing out of washer 10 through line 13 goes into the extractor 15. The 3-cyanopyridine and the 3-methylpyridine present in a given case is extracted here with an organic solvent entering through line 14. The 3-cyanopyridine and the 3-methylpyridine which are in the extract go via line 16 and are recovered by distillation. The organic solvent resulting returns via line 14 to the extraction unit. Loss of organic solvent is compensated for by addition of fresh solvent. The aqueous solution remaining after the extraction 15 goes via line 17 into the desorption unit 20 where carbon dioxide and water are driven off via line 21. Water is led into the desorption unit 20 via line 19. The aqueous residual solution in line 12 from desorption unit 20 is supplied as wash liquid into the gas washer 10 of the first step or stage.

The residual gas in line 31 from the gas washer 10 in the first step is led to the gas washer 30 of the second step or stage, which gas washer 30 is operated at a temperature 10° to 30° C. lower than that at which gas washer 10 of the first step is operated. Water in line 36 freed in desorption unit 35 from ammonia is led to the gas washer 30 as wash liquid. The residual gas in line 34 remaining after the washing in 30 is discarded. The aqueous ammonia solution in line 32 flowing out of the gas washer is led to the desorption unit 35 for driving off the ammonia. The ammonia driven off in line 37 is returned to the reaction.

To establish and maintain stationary ratios in the case of continuous operation it can be necessary because of fluctuations in the composition and the temperature of the reaction gas to branch off a small part of the liquid in line 12 flowing from unit 20 and to mix it in via line 33 with liquid running out of 30 via line 32 and/or discard via line 22. It can also be necessary to branch off a small portion of the liquid flowing out of unit 35 via line 36 and to deliver it via line 18 into unit 20 entirely or partially in place of water 19 and/or to discard as waste water via line 38.

Unless otherwise indicated all parts and percentages are by weight.

The process can comprise, consist essentially of, or consist of the step set forth with the stated materials.

Example

There were used a device built according to the drawings. The gas washers 10 and 30 consisted of packed columns. There were reacted hourly in a preconnected reactor a gaseous mixture of 4800 normal liters of air, 13.5 kg of water, 12.7 kg of ammonia, and 11.0 kg of 3-methylpyridine. A portion of the gaseous mixture hourly consisting of 8.1 kg of ammonia and 12.6 kg of water was waste gas in line 37 from the desorption unit 35. The reaction took place on a solid bed catalyst which was prepared according to German OS No. 3107755 Example 1 (and the related Beschke U.S. application Example 1). Specifically the catalyst is made by suspending 23.3 kg of antimony trioxide, 4.7 kg of ammonium metavanadate, 12.8 kg of titanium dioxide, 11.7 kg of montmorillonite and 5.8 kg of highly dispersed silica having a surface area of 200m$^2$/g in 140 liters of water. Then there is added 16.4 liters of 54% nitric acid. The mixture is slowly heated to the boiling temperature, treated with 7 liters of water, and held for 2 hours at the boiling temperature, then adjusted to a pH of 4.6 with ammonia, cooled, dried on a roller drier, heated in a tubular rotary drier to 300° C. and ground in a spike mill to a particle size below 0.5 mm. 4500 grams of the thus prepared catalyst mixture is intensively mixed with 225 grams of graphite and 1700 grams of a 20% aqueous urea solution and then shaped to extruded briquettes having a diameter of 3 mm. The briquettes are heated on an air stream and held hereby for 15 hours at 120° C., 2 hours at 550° C., 1 hour at 650° C., and 3 hours at 770° C. The bulk density of the catalyst is 1.05 kg 1, the BET surface area 18 m$^2$/g, the macropore volume 0.28 cm$^3$/g and the average pore radius $2.7 \times 10^{-7}$cm.

The gaseous mixture in line 11 formed in the reaction hourly contains essentially 84.4 kg of nitrogen, 14.4 kg of oxygen, 22.9 kg of water, 9.0 kg of ammonia, 1.1 kg of 3-methylpyridine, 9.9 kg of 3-cyanopyridine and 4.5 kg of carbon dioxide.

The gaseous mixture from line 11 was washed hourly in the gas washer 10 of the first step with 129.5 kg of the solution 12 from desorption unit 20 at 50° C. The solution contains hourly 9.9 kg of ammonia and 4.6 kg of carbon dioxide. There were obtained from the gas washer 10 hourly 165.7 kg of solution 13. It contained hourly 12.3 kg of ammonia, 1.1 kg of 3-methylpyridine, 9.9 kg of 3-cyanopyridine and 8.9 kg of carbon dioxide.

The solution was extracted hourly in the extraction 15 with 93.1 kg of benzenes from line 14. The extract 16 contains hourly 9.8 kg of 3-cyanopyridine, corresponding to a yield of 99% based on the 3-cyanopyridine supplied with the gaseous mixture 11 and besides 1.5 kg of 3-methylpyridine. The extract was fractionally distilled to recover 3-cyanopyridine and 3-methylpyridine as well as for recovery of the benzene. The benzene was led back into the extraction and replenished hourly with 0.4 kg of fresh benzene.

Carbon dioxide was driven out of the aqueous phase 17 from the extraction unit 15 in the desorption unit 20 at 8 bar and 145° C. The waste gas 21 contains hourly 3.3 kg of carbon dioxide and besides 0.3 kg of ammonia, 1.9 kg of water, 0.1 kg of 3-cyanopyridine and 0.4 kg of benzene. There were fed hourly to the desorption unit 20 7.9 kg of water via line 18. The residual solution 12 which discharged from the desorption unit 20, contains hourly 139.5 kg of water, 12.0 kg of ammonia and 5.6 kg of carbon dioxide. A portion of 82.5% was taken from it as wash liquid and delivered into the first gas washer 10. The remaining portion of 17.5% was supplied via line 33 to the desorption unit 35.

The second gas washer 30 was operated at 35° C. The residual gas from the first gas washer 10 was led via line 31 to the second gas washer. The residual gas contains hourly 6.6 kg of ammonia besides 0.2 kg of carbon dioxide. This gas was washed in gas washer 30 with 96.0 kg hourly of water from line 36 which water was freed from ammonia in desorption unit 35. The waste gas 34 from the gas washer 30 contains hourly 0.6 kg of ammonia. Together with the waste gas 21 from desorption unit 20 it was led to a combustion furnace.

The wash liquid 32 from the second gas washer 30 contains hourly 6.0 kg of ammonia and 0.2 kg of carbon dioxide. It was led to the desorption unit 35 and here at 2.2 bar and 108° C. freed from ammonia. The liquid in line 36 which was drawn off from the desorption unit was as good as free from ammonia and carbon dioxide. Hourly a portion of 4.9 kg was rejected as waste water 38, another portion was delivered via line 18 to the desorption unit 20 and the remainder supplied to the second gas washer 30 as wash liquid. The gas 37 which accrued from the desorption unit 35 contains hourly 12.6 kg of water, 8.1 kg of ammonia and 1.2 kg of carbon dioxide. It was returned to the reactor.

What is claimed is:

1. In a process for the recovery of 3-cyanopyridine from the gaseous mixture resulting from the catalytic reaction of 3-methylpyridine with ammonia and oxygen and treatment of the gaseous mixture with water, the improvement comprising in a first step treating the gaseous mixture at a temperature of about 30° to 60° C. with water and then in a second step treating the gaseous mixture remaining after the first step with water at a temperature between around 10° to 30° C. lower than the temperature in the first step.

2. A process according to claim 1 wherein the gaseous mixtures in the first and second steps are treated with circulating aqueous solutions.

3. A process according to claim 2 wherein the temperature in the first step is 35° to 55° C. and in the second step is 15° to 25° C. lower than in the first step.

4. A process according to claim 1 wherein the temperature in the first step is 35° to 55° C. and in the second step is 15° to 25° C. lower than in the first step.

5. A process according to claim 4 wherein the wash liquid in the first step is saturated or substantially saturated with ammonia.

6. A process according to claim 2 wherein the wash liquid in the first step is saturated or substantially saturated with ammonia.

7. A process according to claim 1 wherein the gaseous mixture treated in the first step contains 3-cyanopyridine, ammonia, carbon dioxide, nitrogen, and oxygen.

8. A process according to claim 7 wherein the wash liquid in the first step is saturated or substantially saturated with ammonia.

9. A process according to claim 7 wherein the wash water is so regulated that per mole of carbon dioxide in the gases being treated there are present at least about 3 moles of ammonia and per mole of ammonia there is about 0.1 to 0.5 mole of water.

10. A process according to claim 9 wherein there are present in the wash water at least about 5 moles of ammonia per mole of carbon dioxide in the gases being treated.

11. A process according to claim 1 wherein the gaseous mixture results from the catalytic reaction of 3-methylpyridine with ammonia and oxygen and the catalyst is (1) tin vanadate in admixture with phosphorus pentoxide or aluminum oxide, silica gel or their mixture, (2) molybdenum oxide in admixture with an oxide of vanadium, chromium, manganese or cobalt on aluminum oxide, magnesium oxide, silica or titanium dioxide, (3) pure vanadium pentoxide, (4) a catalyst prepared by treating by heating to temperatures of 600° to 1100° C. in the presence of oxygen a mixture which contains at least one of the elements titanium, iron, copper, cobalt, manganese, or nickel or (5) a catalyst consisting essentially of the elements antimony, vanadium and oxygen and additionally at least one of the elements iron, copper, titanium, cobalt, manganese, and nickel where the atomic ratio of antimony to vanadium is greater than 1 and which contains in addition to these compounds a lattice layer silicate and highly dispersed silica and which has a BET surface area of 5 to 50 $m^2/g$, a macropore volume of 0.1 to 0.8 $cm^3/g$, and an average pore radium of 1 to $8 \times 10^{-7}$ cm.

12. A process according to claim 11 where the catalyst in the catalytic reaction was (1).

13. A process according to claim 11 where the catalyst in the catalytic reaction was (2).

14. A process according to claim 11 where the catalyst in the catalytic reaction was (3).

15. A process according to claim 11 where the catalyst in the catalytic reaction was (4).

16. A process according to claim 11 where the catalyst in the catalytic reaction was (5).

17. A process according to claim 16 wherein in the catalyst the atomic ratio of antimony to vanadium is between 1.1 to 1 and 50:1, the atomic ratio of antimony to said additional element when it is iron, cobalt, copper, manganese, or nickel is between 2 to 1 and 20 to 1 with the proviso that the atomic portion of said additional element does not exceed that of vanadium and when the additional element is titanium, the atomic ratio of antimony to titanium is between 1 to 3 and 8 to 1, the mixture of lattice layer silicate and highly dispersed silica is about 10 to 60 weight %, the ratio of lattice layer silicate to highly dispersed silica is between about 20 to 1 and 0.25 to 1 parts by weight and the silica has a BET surface area of about 50 to 500 m²/g.

18. A process according to claim 17 wherein in the catalyst the atomic ratio of antimony to vanadium is between 1.1 and 25 to 1, the atomic ratio of antimony to said additional element when it is iron, cobalt, copper, manganese, or nickel is between 3 to 1 and 10 to 1 and when the additional element is titanium the atomic ratio of antimony to titanium is between 1 to 2 and 4 to 1, the mixture of lattice layer silicate and highly dispersed silicate is 20 to 40 weight percent, the ratio of lattice layer silicate to highly dispersed silica is between 10 and 1 and 1 to 1 and the highly dispersed silica has a BET surface area of about 100 to 300 m²/g.

19. A process according to claim 11 wherein the catalytic reaction had been carried out at 320° to 460° C.

20. A process according to claim 1 wherein the catalytic reaction has been carried out at 320° to 460° C.

* * * * *